(12) United States Patent
Remmereit et al.

(10) Patent No.: US 6,440,931 B1
(45) Date of Patent: Aug. 27, 2002

(54) CONJUGATED LINOLEIC ACID IN TREATMENT AND PROPHYLAXIS OF DIABETES

(75) Inventors: Jan Remmereit, Volda; Jan Wadstein; Jo Klaveness, both of Oslo, all of (NO)

(73) Assignee: Natural Corporation, Sandvira (NO)

( * ) Notice: Subject to any disclaimer, the term of this patent is extended or adjusted under 35 U.S.C. 154(b) by 0 days.

(21) Appl. No.: 09/510,059

(22) Filed: Feb. 22, 2000

Related U.S. Application Data

(60) Provisional application No. 60/121,232, filed on Feb. 23, 1999.

(51) Int. Cl.[7] ............................................... A61K 38/28
(52) U.S. Cl. ................... 514/3; 514/3; 514/2; 514/560; 514/549; 514/558; 426/630; 426/2; 426/807
(58) Field of Search ............................... 514/2, 3, 560, 514/549, 558; 426/630, 2, 807

(56) References Cited

U.S. PATENT DOCUMENTS

| | | | |
|---|---|---|---|
| 4,472,432 A | 9/1984 | Iwamura et al. | 424/318 |
| 4,681,896 A | 7/1987 | Horrobin | 514/552 |
| 4,806,569 A | 2/1989 | Horrobin | 514/552 |
| 4,826,877 A * | 5/1989 | Stewart et al. | 514/560 |
| 4,868,212 A | 9/1989 | Horrobin | 514/25 |
| 5,034,415 A | 7/1991 | Rubin | 514/560 |
| 5,428,072 A | 6/1995 | Cook et al. | 514/560 |
| 5,430,066 A | 7/1995 | Cook et al. | 514/558 |
| 5,496,735 A | 3/1996 | Schwertner | 436/71 |
| 5,554,646 A | 9/1996 | Cook et al. | 514/560 |
| 5,585,400 A | 12/1996 | Cook et al. | 514/560 |
| 6,015,833 A | 1/2000 | Saebo et al. | 514/558 |
| 6,034,132 A | 3/2000 | Remmereit | 514/560 |
| 6,042,869 A | 3/2000 | Remmereit | 426/630 |
| 6,060,514 A | 5/2000 | Jerome et al. | 514/560 |

FOREIGN PATENT DOCUMENTS

WO     WO 99/29317    * 6/1999

OTHER PUBLICATIONS

Houseknecht et al., Biochemical and Biophysical Research Communications, vol. 244, pp. 678–682, 1998.*
Sebedio et al., Current Opinion in Clinical Nutrition and Metabolic Care, vol. 2, pp. 499–506, 1999.*
Berdeaux et al., JAOCS, vol. 74, No. 8, pp. 1011–1015, 1997.*
Cook et al., International Dairy Journal, vol. 8, pp. 459–462, 1998.*
Gumbirer et al., *Diabetes Care*, 21:9–15 (1998).
Santini et al., *Diabetes*, 46:1853 (1997).
Leonthardt, et al., *Clin. Chim. Acta.*, 254:173–86 (1996).
Houseknecht et al., *Biochem, Biophys. Res. Commun.*, 244:678–82 (1998).
Chin et al., *J. Food Comp. Anal.*, 5:185–197 (1992).
West, et al., *Am. J. Physiol.*, 275:R667–72 (1998).
Lee et al., *Atherosclerosis*, 108, 19–25 (1994).
Belury, et al., *Nut. Rev.*, 53(4):83–9 (1995).
Cesano, *Anticancer Res.*, 18:1429–34 (1998).
Thompson, *Cancer Res.*, 57:5067–72 (1997).
Liu et al., *Lipids*, 32:725–30 (1997).
Durgam et al., *Cancer Lett.*, 116:121–30 (1997).
Wong, *Anticancer Res.*, 17:987–93 (1997).
Ip et al., *Carcinogenesis*, 18:755–9 (1997).
Cowen, *JAOCS*, 72:492–99 (1950).
Gabbay, *N. Engl. J. Med.*, 295:443–4 (1976).
Koenig et al., *N. Engl. J. Med.*, 295:417–20 (1976).
Lie Ken Jie and Mustafa, *Lipids*, 32 (10) 1019–24 (1997).

* cited by examiner

*Primary Examiner*—Karen Cochrane Carlson
*Assistant Examiner*—Hope A. Robinson
(74) *Attorney, Agent, or Firm*—Medlen & Carroll, LLP

(57) ABSTRACT

This invention provides method of treatment and prophylaxis of both insulin (Type I) and non-insulin dependent (type II) diabetes mellitus, by administration of conjugated linoleic acid (CLA) in the form of pure isomers, selected isomer mixtures or non-selected isomer mixtures. The conjugated linoleic acids may be administered alone, or in combination with other diabetes therapeutic regimes.

46 Claims, No Drawings

CONJUGATED LINOLEIC ACID IN TREATMENT AND PROPHYLAXIS OF DIABETES

This is a Divisional of copending application Ser. No. 60/121,232, filed on Feb. 23, 1999.

FIELD OF THE INVENTION

This invention provides a method for treatment and prophylaxis of diabetes comprising administering conjugated linoleic acid to subjects suspected of suffering from or at risk of developing diabetes.

BACKGROUND

Diabetes mellitus is a chronic metabolic disorder characterized by a high concentration of glucose in blood (hyperglycemia) which is a result of insulin deficiency and/or insulin resistance. Diabetes is a common disease in humans, with more than 50 million cases worldwide. There are two main forms of diabetes, insulin-dependent diabetes mellitus (e.g., Type I diabetes) and non-insulin dependent diabetes mellitus (e.g., Type II diabetes).

Insulin is the main form of treatment of Type I diabetes and has to be administrated parenterally (e.g., by injection). Today, most of the insulin in clinical use is produced recombinantly. Type II diabetes can be treated with various oral anti-hyperglycemic agents like biguanidines (e.g., metformin), sulphonylurea compounds such as tolbutamide, chlorpropamide, glipizid and glibenclamide, and acarbose (i.e., an alpha-glucosidase inhibitor). Very mild forms of diabetes mellitus (Type II) can often be kept under control by the patient without use of drugs by selection of correct diet (e.g., intake of limited amounts of carbohydrates), bodyweight reduction for obese patients, increased exercise and reduction of stress.

Anti-diabetic drugs only provide symptomatic relief and do not cure the disease. Thus, affected patients usually undergo treatment for the rest of their lives. Anti-diabetic drugs have several unwanted effects such as stimulation of appetite resulting in gain of body weight, hypoglycemia, gastrointestinal upsets, allergic skin reactions, bone marrow damage and cardiovascular effects. (See, e.g., Godman and Gilman's "The Pharmacologocal Basis of Therapeutics", 9$^{th}$ edition and "H. P. Rand et al., Pharmacology 1995", Churchill Livingstone).

Research continues in the development of improved drugs and treatment regimens. Of particular interest is the development of drugs with increased safety and efficacy. Ongoing concerns include the detrimental interactions of current anti-diabetic drugs with other medications in common use (e.g., anti-inflammatory agents), development of drug resistance and/or tolerance, and patient compliance with prescribed treatment regimes.

What is needed are safe and effective compounds for treating diabetes that lack significant side effects and can be consumed as part of the normal diet.

SUMMARY OF THE INVENTION

An important challenge in modern medicine is to devise safe and effective methods of treating diabetes. It is therefore an object of the present invention to provide a safe method of treating Type I and Type II diabetes through the use of a naturally occurring substance, conjugated linoleic acid (CLA). Accordingly, the present invention provides methods for the use of CLA in treatment and prophylaxis of diabetes.

In one embodiment of the present invention, methods are provided for treating diabetes in human patients suffering from diabetes that comprises administering a safe and therapeutically effective amount of conjugated linoleic acid. In some embodiments, the patients suffer from Type I diabetes, while in other embodiments, patients suffer from Type II diabetes. In some preferred embodiments, a safe and effective amount is sufficient to reduce the percentage of glycoslylated hemoglobin ($HbA_{IC}$) in the patient's blood. In some embodiments, the method of treatment comprises: a) providing i) a safe and therapeutically effective amount of conjugated linoleic acid; and ii) a patient suffering from diabetes; and b) administering said safe and therapeutically effective amount of conjugated linoleic acid to said diabetic patient. In other embodiments, the method of treatment comprises providing: i) a patient at risk for diabetes, and ii) a therapeutic composition comprising a safe and effective amount of conjugated linoleic acid; and b) prophylactically administering the therapeutic composition to said patient.

In some embodiments of the invention, the conjugated linoleic acid administered to patients is a mixture of octadecadienoic acid isomers selected from the group of cis-9, trans-11; cis-9, cis-11; trans-9, cis-11; trans-9, trans-11; cis-10, cis-10, trans-12; trans-10, cis-12; trans-10, trans-12 octadecadienoic acid. In other embodiments, the conjugated linoleic acid administered to patients contains less than 5% of minor isomers of conjugated linoleic acid. In still other embodiments, the minor isomer is c11,t13; t11,c13; t11,t13; or c11,c13 octadecadienoic acid. In a particularly preferred embodiment, the conjugated linoleic acid contains less than 1% of minor isomers of conjugated linoleic acid. In other embodiments, the conjugated linoleic acid further comprises an ester or triglyceride. In still other embodiments, the conjugated linoleic acid further comprises greater than about 55% t10,c12 octadecadienoic acid.

In other embodiments of the present invention, the conjugated linoleic acid comprises a daily dosage of about 0.05 to 40 grams. In some particularly preferred embodiments, the conjugated linoleic acid comprises a daily dosage of about 1 to 5 grams. In some embodiments, the conjugated linoleic acid is administered orally in a gel capsule. In other embodiments, the conjugated linoleic acid is provided as a supplement to a low carbohydrate diet. In still other embodiments, the conjugated linoleic acid is provided in a food product (e.g., prepared food or drink).

In some embodiments, the conjugated linoleic acid is co-administered with an anti-hyperglycemia agent. In other embodiments, the anti-hyperglycemia agent is selected from the group consisting of insulin, metformin, chorplopamide, glipizid, glibenclamide and acarbose.

DEFINITIONS

The following definitions are provided to make the invention be more easily understood:

As used herein, "diabetes" refers to any disease characterized by a high concentration of glucose in blood (hyperglycemia) and includes, but is not limited to, both Type I diabetes mellitus and Type II diabetes mellitus.

As used herein, "Type I diabetes" refers to any insulin dependent diabetes disease.

As used herein, "Type II diabetes" refers to any non-insulin diabetes disease.

As used herein, "patient at risk for diabetes" refers to any person having risk factors known in the art for Type I diabetes (e.g., family history, descent (African or hispanic), etc.) or Type II diabetes (e.g., family history, age (over 45), obesity, previous diagnosis of impaired glucose tolerance, physical inactivity, etc.).

As used herein, "conjugated linoleic acid" or "CLA" refers to any conjugated linoleic acid or octadecadienoic acid. It is intended that this term encompass and indicate all positional and geometric isomers of linoleic acid with two conjugated carbon-carbon double bonds any place in the molecule. CLA differs from ordinary linoleic acid in that ordinary linoleic acid has double bonds at carbon atoms 9 and 12. Examples of CLA include cis- and trans isomers ("E/Z isomers") of the following positional isomers: 2,4-octadecadienoic acid, 4,6-octadecadienoic acid, 6,8-octadecadienoic acid, 7,9 - octadecadienoic acid, 8,10-octadecadienoic acid, 9,11-octadecadienoic acid and 10,12 octadecadienoic acid, 11, 13 octadecadienoic acid. As used herein, CLA encompasses a single isomer, a selected mixture of two or more isomers, and a non-selected mixture of isomers obtained from natural sources, as well as synthetic and semisynthetic CLA. As used herein, CLA further encompasses free fatty acid(s) of CLA, physiologically acceptable salts of CLA, and esters with physiologically acceptable, preferably naturally occurring, alcohols ( e.g., ethanol and glycerol).

As used herein, it is intended that "triglycerides" of CLA contain an isomer of CLA at any or all of three positions on the triglyceride backbone. Methods for the synthesis of triglycerides containing CLA are taught in PCT Application US99/05806, incorporated herein by reference.

As used herein, it is intended that "esters" of CLA include any CLA isomer bound through an ester linkage to an alcohol or any other chemical group. Methods for the synthesis of esters containing CLA are taught in PCT Application US99/05806, incorporated herein by reference.

It is intended that "minor isomers" of CLA include, but are not limited to c11,t13; t11,c13; t11,t13; and c11,c13 octadecadienoic acid. "Prepared food product" means any pre-packaged food approved for human consumption.

As used herein, "c" encompasses a chemical bond in the cis orientation, and "t" refers to a chemical bond in the trans orientation. If a positional isomer of CLA is designated without a "c" or a "t", then that designation includes all four possible isomers. For example, 10,12 octadecadienoic acid encompasses c10,t12; t10,c12; t10,t12; and c10,c12 octadecadienoic acid.

DESCRIPTION OF THE INVENTION

This invention provides a method for treatment and prophylaxis of diabetes comprising administering conjugated linoleic acid to subjects suspected of suffering from or at risk of Developing diabetes. Insulin is commonly used to treat diabetes and acts by regulating carbohydrate metabolism. In addition to carbohydrate metabolism, insulin also has several effects on the metabolism of fat and fatty acids that are of concern in patients with diabetes. For example, insulin increases the synthesis of fatty acids and triglycerides in adipose tissue. U.S. Pat. No. 5,496,735 (herein incorporated by reference) discloses a method of determination of patient risk for diabetes based on lipid fatty acid in serum.

There are several reports that document an increased amount of conjugated fat compounds in the tissues of diabetic patients. Inouye et al. have shown a significant increase in the ratio of CLA to linoleic acid in human diabetic erythrocytes compared with control erythrocytes. (Inouye et al., *Clin. Chim. Acta.*, 287:163–72 (1998)). An increased CLA (9,11 isomer) to linoleic acid ratio in diabetic rats has also been demonstrated. (al-Zuhav et al., *Pharmacol. Res.*, 38:59–64 (1998)). Another report on oxidative stress and metabolic control in non-insulin dependent diabetes mellitus (NIDDM) indicated that hypoglycemic agents substantially lower concentration of cis, trans and trans conjugates dienes in low-density lipoprotein esters and triglycerides. (Singh et al., *Indian J. Biochem. Biol.*, 512:17 (1998)). The concentrations of these dienes were found to be significantly higher in subjects with NIDDM than in subjects with normal glucose tolerance. Gumbirer et al. have shown that mono-unsaturated fatty acid enriched hypocaloric diets potentiate the beneficial effects of weight loss and improve cardiovascular risk factors in obese patients with type II diabetes. (Gumbirer et al., *Diabetes Care*, 21:9–15 (1998)). Additional reports indicate that increased levels of conjugated dienes occur in blood plasma in patients with diabetes. (See, e.g., Santini et al., *Diabetes*, 46:1853 (1997); Zhang, et al., *Arterioscler. Thromb. Vasc. Bid*, 18:1140–48 (1998); Khajanachumpol, et al., *J. Med. Assoc. Thai.*, 80:372–77 (1998); Leonthardt, et al., *Clin. Chim. Acta.*, 254:173–86 (1996); and Dimitiradis, *J. Am. Geriatric. Soc.*, 39:571–4 (1991)). In contrast, Colier et aL, *Diabetic Med.*, 5:747–9 indicate that the concentration of CLA is reduced in insulin-dependent diabetic patients. Thus, there are conflicting reports in the literature regarding the CLA levels in diabetic patients.

Fatty acid metabolites of linoleic acid and linolenic acid have been suggested for use in the treatment of diabetes, as well as several other severe diseases. (See, e.g., U.S. Pat. Nos. 4,681,896; 4,806,569; and 4,868,212, incorporated herein by reference). However, the use of conjugated linoleic acids is not described in these patents. U.S. Pat. No. 5,034,415 (each incorporated herein by reference) discloses a method for treating diabetes mellitus comprising administering isomers of eicosapentaenoic acid (EPA) or 22:6 omega -3 docosahexaenoic acid (DHA). U.S. Pat. No. 4,472,432 (herein incorporated by reference) discloses a method of treating diabetes comprising administration of "alpha" and "beta" unsaturated fatty acids and Houseknecht et al., *Biochem. Biophys. Res. Commun.*, 244:678–82 (1998) indicate that CLA is able to normalize impaired tolerance and improve hyperinsulinemia in an animal model (i.e., pre-diabetic Zucker diabetic rats).

Conjugated linoleic acid has been identified in meat and dairy products (Chin et al., *J. Food Comp. Anal.*, 5:185–197 (1992)). CLA has several unique properties when used as a food additive or dietary supplement. U.S. Pat. No. 5,554,646 (herein incorporated by reference) discloses the use of CLA to reduce the percentage of fat in relation to total body mass. Other publications describe a variety of physiological effects caused by CLA including reduction in body fat, changes in energy metabolism, and changes in cardiovascular health indicators. (See, e.g., Wast, et al., *Am. J. Physiol.*, 275:R667–72 (1998), and Lee et al., *Atherosclerosis*, 108, 19–25 (1994).

U.S. Pat. No. 5,428,072 (incorporated herein by reference) discloses the use of CLA for increasing the efficiency of feed conversion in animals, which results in more non-fat tissue being formed in relation to weight gain. U.S. Pat. Nos. 5,430,066 and 5,585,400 (both incorporated herein by reference) disclose the use of CLA to prevent weight loss due to immune stimulation and to treat immune hypersensitivity. CLA also has anticarcinogenic activity. (See, e.g., Belury, *Nut. Rev.*, 53(4):83–9 (1995); Santoli, *Anticancer Res.*, 18:1429–34 (1998); Thompson, *Cancer Res.*, 57:5067–72 (1997); Liu et al., *Lipids*, 32:725–30 (1997); Durgam et al., *Cancer Lett.*, 116:121–30 (1997); Ip et al., *Carcinogenesis*, 18:755–9 (1997); and Wong, *Anticancer Res.*, 17:987–93 (1997).

The mechanism by which CLA mediates these effects is not known, and indeed an understanding of the mechanism is not necessary in order to use the invention. Nonetheless, some biochemical models involving fat partitioning and shifts in fatty acid precursor mediated synthesis of end product prostaglandins and leukotrienes have been proposed. For example, it is known that CLA is taken up in triglycerides and phospholipids, and deposited in fat stores. The precise structure and distribution of these lipids is not known. Nor is it known whether there is a competitive incorporation amongst two or more isomers, or a preferential deposition of certain isomers in some lipid species over others. Such an understanding is not required in order to use the present invention.

In preferred embodiments, the CLA of the present invention comprises a mixture of one or all of the isomers of octadecadienoic acid including the cis-9, trans-11; cis-9, cis-11; trans-9, cis-11; trans-9, trans-11; cis-10, cis-12; cis-10, trans-12; trans-10, cis-12; and trans-10, trans-12 isomers. The rearrangement of the double bonds of linoleic acid to conjugated positions has been shown to occur during treatment with catalysts such as nickel or alkali at high temperatures, and during autooxidation. Theoretically, eight possible geometric isomers of 9,11 and 10,12 octadecadienoic acid (i.e., c9,c11; c9,t11; t9,c11; t9,t11; c10,c12; c10,t12; t10,c12 and t10,t12) would form from the isomerization of c9,c12-octadecadienoic acid.

A general mechanism for the isomerization of linoleic acid was described by Cowan (Cowen, *JAOCS*, 72:492–99 (1950)). Although an understanding of the mechanism is not required for the practice of the present invention, it is believed that the double bond is polarized by the result of a collision with an activating catalyst. The polarized carbon atom and its adjoining carbon are then free to rotate and the forces are such as to make the deficient carbon atom essentially planar. When the system reacts to relieve these forces set up as a result of the collision, both cis and trans isomers are formed. The formation of certain isomers of CLA is thermodynamically favored. This is due to the co-planar characteristics of the five carbon atoms around the conjugated double bond and a spatial conflict of the resonance radical.

Although an understanding of this mechanism is not required for the practice of the present invention, the relatively higher distribution of 9,11 and 10,12 isomers apparently results from the further stabilization of the c9,t11or t10,c12 geometric isomers. The cis-9,trans-11 and trans-10, cis-12 isomers are thought to have the most biological activity. Therefore, in preferred embodiments, these isomers may be used in a purified form, or in CLA compositions containing high ratios of these isomers. Most preferably, the CLA composition used in the present methods is TONALIN™CLA 80 (Natural Nutrition, Norway). In addition, methods for manufacturing CLA 80 are provided in Example 2 (i.e., low temperature nonaqueous alkali isomerization) and an alternative method of manufacturing another preferred CLA composition is provided in Example 3 (i.e., isomerization with alkali alcoholate in the presence of a monohydric low molecular weight alcohol). Both methods provide for the production of CLA predominantly comprising the c9,t11- and t10,c12- isomers, with low levels of 8,10-,11,13- and trans-trans isomers. In preferred embodiments of the present invention, CLA mixtures contain less than about 5% of minor CLA isomers; while in particularly preferred embodiments, the present invention utilizes CLA with less than about 1% of minor CLA isomers. Preferred isomers in the CLA mixtures include 9,11 -octadecadienonic acid, 10,12- octadecadienoic acid, most preferably the c9,t11 and t10,c12 isomers. In other preferred embodiments, the mixture contains greater than about 50% t10,c12 isomer. In other particularly preferred embodiments, the mixture contains greater than about 55% t10,c12 isomer. In a particularly preferred embodiment, the mixture contains greater than about 60% t10,c12 isomer. It is contemplated that in some embodiments, supplementation of the mixture derived from isomerization of linoleic acid with purified or synthesized t10,c12 isomer may be necessary to achieve these percentages.

In a preferred embodiment of the present invention, a safe and therapeutically effective amount of CLA is orally administered to a human with diabetes. The use of CLA for these indications is desirable because CLA is a non-toxic, naturally occurring food ingredient. CLA is not classified as a drug and may be consumed as a part of a normal diet and finds use as a part of everyday nutrition. In a preferred embodiment, the CLA may be used as a fatty acid supplement for the low carbohydrate diets often prescribed for diabetic patients.

A "therapeutically effective amount" of CLA is the amount of CLA that, when ingested in purified form or as food supplement, results in an improvement of Type II diabetes symptoms without impairing or interfering with proper nutrition. In particularly preferred embodiments, the administration of CLA results in no detrimental effects in patients. In some embodiments, about 0.05 to 40 grams of CLA may be administered per day, preferably about 1 to 10 grams per day may be administered, and most preferably about 3.0 grams per day may be administered. In general, the amount of CLA administered is not critical, as long as it is enough to be therapeutically effective. The amounts of CLA deemed therapeutically effective are those which result in a measurable decrease in $HbA_{IC}$ (i.e., glycosylated hemoglobin) when administered over a three month period or longer. $HbA_{IC}$ is useful as an index of hyperglycemic stress, and is elevated in patients with poorly managed diabetes. The glycation of $HbA_{IC}$ is a non-enzymatic, post-translational event linked to elevated levels of glucose in the blood. $HbA_{IC}$ levels may be determined as is known in the art by HPLC. (See, e.g., Inonye et al., *Clin. Chim. Acta.*, 295:163–72 (1998); Gabbay, *N. Engl. J. Med.*, 295:443–4 (1976); Koenig et al., *N. Engl. J. Med.*, 295:417–20 (1976)).

It is contemplated that there will be some variation in effectiveness due to differences among individuals in physiological and biochemical parameters (e.g., body weight and basal metabolism), exercise, and other aspects (e.g., diet). It is contemplated that individuals beginning treatment will be given a 3.0 gram dose for an initial two month period, and then, if no reduction serum glucose is experienced, gradually increase the CLA dose up to about 10 grams per day.

The present invention also contemplates the use of derivatives of CLA. For example, CLA may be free or bound through ester linkages or provided in the form of an oil containing CLA triglycerides. In these embodiments, the triglycerides may be partially or wholly comprised of CLA attached to a glycerol backbone. The CLA may also preferably be provided as a methylester or ethylester. Furthermore, the CLA may be in the form of a non-toxic salt, such as a potassium or sodium salt (e.g., a salt formed by reacting chemically equivalent amounts of the free acids with an alkali hydroxide at a pH of about 8 to 9).

In one preferred embodiment, administration is oral. The CLA may be formulated with suitable carriers such as starch, sucrose or lactose in tablets, pills, dragees, capsules, solutions, liquids, slurries, suspensions and emulsions. The CLA may be provided in aqueous solution, oily solution, as a powder, or in any of the other forms discussed above. The tablet or capsule of the present invention may be coated with an enteric coating which dissolves at a pH of about 6.0 to 7.0. A suitable enteric coating which dissolves in the small intestine but not in the stomach is cellulose acetate phthalate. In a preferred formulation, the CLA is provided as soft gelatin capsules containing 750 mg 80% CLA (TONALIN™). In another preferred embodiment, the CLA is provided as a powder contained in a capsule. The CLA may 5 also be provided by any of a number of other routes, including, but not limited to, intravenous, intramuscular, intra-arterial, intramedullary, intrathecal, intraventricular, transdermal, subcutaneous, intraperitoneal, intranasal, enteral, topical, sublingual or rectal means. Further details on techniques for formulation for and administration and administration may be found in the latest edition of *Remington's Pharmaceutical Sciences* (Maack Publishing Co., Easton, Pa.).

An effective amount of CLA may also be provided as a supplement in various prepared food products and drinks. For the purposes of this application, prepared food product means any natural, processed, diet or non-diet food product to which CLA has been added. The CLA may be added in the form of free fatty acids or as an oil containing partial or whole triglycerides of CLA. Therefore, CLA may be directly incorporated into various prepared food products, including, but not limited to diet drinks, diet bars, supplements, prepared frozen meals, candy, snack products (e.g., chips), prepared meat products, milk, cheese, yogurt and any other fat or oil containing foods.

In some preferred embodiments, CLA is used in combination with anti-hyperglycemic agents. Examples of such agents with which CLA can be combined include insulin, metformin, chorplopamide, glipizid, glibenclamide and/or acarbose. In still other embodiments, CLA may be used in combination with vanadium compounds, chromium compounds, lipoic acid, AGE inhibitors/breakers or other compounds with known positive effect on relieving the symptoms associated with diabetes.

CLA is susceptible to oxidation. Therefore, it is desirable to package CLA for human use with suitable antioxidants such as lecithin, tocopherols, ascorbate, ascorbyl palmitate or spice extracts such as rosemary extract.

EXAMPLES

The following examples serve to illustrate certain preferred embodiments and aspects of the present invention and are not to be construed as limiting the scope thereof.

Example 1

CLA Capsules As Dietary Supplement For Type 2 Diabetes

In this Example, CLA capsules were administered and the effect of CLA on the patient's symptoms analyzed. The patient received TONALIN™ capsules (80% CLA), 4 capsules of 750 mg, daily for 12 weeks. Laboratory data at the start and end of the study indicated that CLA had a positive effect on reducing symptoms and signs of diabetes in this patient.

TABLE 1

Laboratory Results

|  | START | END |
|---|---|---|
| $HbA_{1C}$ (%) | 11.4 | 10.3 |
| Serum lipase (U/L) (activity) | 81 | 145 |
| Triglycerides (mmol/L) | 1.73 | 1.02 |
| Total cholesterol (mmol/L) | 6.3 | 4.1 |
| LDL cholesterol (mmol/L) | 4.4 | 2.6 |
| HDL cholesterol (mmol/L) | 1.1 | 1.0 |
| Lp (a) | 128 | 105 |

Table 1 provides the results obtained for various tests conducted prior to the initiation of the treatment ("start") and at the conclusion of the treatment ("end"). These results demonstrate that administration of CLA to this patient had a beneficial effect on the patient's health.

Example 2

Isomerization Of Safflower Oil Using Propylene Glycol At Low Temperature

In this example, isomerization was used to produce isomers of CLA with utility in the invention. Safflower oil was isomerized in propylene glycol at low temperatures using KOH as a catalyst. The isomerization apparatus consisted of a two-necked flask with a thermometer placed in one neck, leaving a small opening to release excess pressure. A nitrogen supply was attached to the other neck of the flask. Solutions added to the flask were agitated by the use of a magnetic bar and a magnetic stirrer. The temperature of the flask was controlled by placing the flask in a thermostat-controlled oil bath placed on the magnetic stirrer.

The flask was filled with 60.27 g propylene glycol and 28.20 g KOH and immersed into the oil bath. The temperature was increased to 130° C. to dissolve the KOH. After the KOH had dissolved, 60.09 g of safflower oil was introduced into the flask. A high volume of nitrogen was circulated through the two-neck flask for 5 min. and then reduced to a lower volume. The mixture was heated to 150° C., which took approximately 40 min. The mixture was then allowed to react at 150° C. for 3.5 hours. At intervals, 3 ml samples were withdrawn for analysis.

The samples withdrawn for analysis were placed directly into 6 ml of hot water and citric acid was added in excess until the free fatty acids separated out as the top layer. Heating was necessary to prevent solidification while the citric acid was added. To convert the free fatty acids into methylesters for analysis by gas chromatography, 0.025 g of the free fatty acids, 5 ml of a 4% solution of HCl, and ethanol were added to a test tube. Nitrogen was added to the tube, then the tube was sealed, and placed in a water bath at 60° C. for 20 min. The tube was then cooled and 1 ml purified water and 5 ml isooctane were added. Nitrogen was added to the tube and the tube was shaken for 30 seconds. The resulting upper layer was added to 1 $\mu$l of purified water in a new test tube and again shaken under nitrogen. The resulting upper layer was then washed of isooctane and decanted into a third test tube. A small amount of sodium sulfate was added to the sample for water absorption. A 1 $\mu$l sample was then injected directly into the gas chromatograph.

The gas chromatography conditions were as follows:

System: Perkin-Elmer Auto System

Injector: Splitless at 240° C.

Detector: Flame Ionization Detector at 280° C.

Carrier: Helium

Column: WCOT Fused Silica 0.25 mm×100 M, CP-SL 88 for FAME, DF 0.2

Oven Program: 80° C. (0 min.) increasing to 220° C. at 10° C. per min. and held at 220° C. for 10 min.

All results are expressed as the relative peak area percentage. Standards are generally unavailable, so the peaks which eluted were verified with other systems. Gas chromatography-mass spectometry (GC-MS) determines the number, but not the position of cis and trans bonds. Therefore, nuclear magnetic resonance (NMR) analysis was used to verify the bond positions. The main peaks identified were c9,t11 and t10,c12 using methods known in the art. (See, e.g., Lie Ken Jie and Mustafa, *Lipids*, 32 (10) 1019–34 (1997), incorporated herein by reference).

The GC data demonstrated that isomerization of safflower oil using polypropylene glycol as a solvent, KOH as a catalyst, and low temperatures results in the production of conjugated linoleic acid lacking 8,10 and 11,13 isomers. The highly polar columns utilized in this experiment may be successfully used to separate the 8,10 and 11,13 isomers from c9,t11 and t10,c12 isomers. The 8,10 isomers tend to coelute or elute just after the c9,t11 isomer. The 11,13 isomer elutes in front of the t10,c11 isomer or coelutes with the t10,c12 isomer, depending on the column conditions. The GC results are summarized in Table 2.

The conjugated linoleic acid (CLA 80) produced according to this method was characterized by comparing the various isomers produced. First, the isomerization reaction went essentially to completion. The completeness of the reaction was determined by dividing the total peak area the for linoleic acid isomers minus residual c9, t12 linoleic acid by the total peak area. This value is 0.994. Second, the ratio of c9,t11 and t10,c12 isomers to total peak area may be determined. This value is 0.953. Third, the ratio of the t9,t11 and t10,t12 isomers to the c9,t11 and t10,c12 isomers may be determined. This value is 0.010. Fourth, the ratio of the t9,t11 and t10,t12 isomers to total peak area may be determined. This value is 0.009. Fifth, the ratio of the t10,c12 isomer to the c9,t11 isomer may be determined. This value is 1.018.

Using the method described in this Example, a high percentage of linoleic acid was converted primarily to the conjugated c9,t11 and t10,c12 isomers in a carefully controlled reaction yielding greater than 90 percent of these isomers, so that less than a combined 1 percent of the 11,13 isomers, less than 1 percent of the 8,10 isomers, less than 1 percent of the double trans species (the t9,t11 and t10,t12 isomers), and less than 1 percent total unidentified linoleic acid species is present in contrast to conventional compositions. Indeed, it is contemplated that the predominance of the c9,t11- and c10,t12- isomers in this composition contributes to its biological effect. In many individual product runs, the final composition has levels of these species virtually undetectable by GC analysis. The 1 percent limit in concentration of the 11,13 and 8,10 isomers serves as a convenient and practical quality assurance standard of purity for a commercial scale manufactured food grade product.

TABLE 2

Gas Chromatography Results

| Peak # | Time (Min) | Component Name | Area (%) | Area ($\mu$V.s) | Height ($\mu$V) |
|---|---|---|---|---|---|
| 1 | 38.164 | | 0.08 | 4101.65 | 622.28 |
| 2 | 49.539 | C16:0 | 6.29 | 335897.80 | 32745.95 |
| 3 | 53.107 | C16:1 | 0.06 | 3240.60 | 447.82 |
| 4 | 61.620 | C18:0 | 2.38 | 127182.30 | 12999.14 |
| 5 | 64.821 | C18:1 c9 | 12.34 | 659111.72 | 52209.40 |
| 6 | 65.254 | | 0.57 | 30402.68 | 3475.09 |
| 7 | 67.263 | | 0.11 | 5757.35 | 758.08 |
| 8 | 67.940 | | 0.10 | 5523.00 | 700.44 |
| 9 | 68.755 | | 0.24 | 12816.90 | 1543.27 |
| 10 | 69.310 | | 0.22 | 11803.80 | 1430.59 |
| 11 | 69.846 | C18:2 c9,c12 | 0.44 | 23336.75 | 2500.24 |
| 12 | 73.618 | | 0.28 | 14828.70 | 1838.66 |
| 13 | 76.621 | | 0.16 | 8400.65 | 1050.19 |
| 14 | 77.388 | CLA c9,t11 | 36.51 | 1950669.98 | 124313.83 |
| 15 | 78.370 | CLA t10,c12 | 37.16 | 1985488.96 | 132265.33 |
| 16 | 78.664 | CLA c9,c11 | 1.06 | 56583.10 | 5699.43 |
| 17 | 78.880 | CLA c10,c12 | 1.26 | 67503.55 | 4572.65 |
| 18 | 80.102 | CLA t9,t11/ t10,t12 | 0.73 | 39110.00 | 4743.28 |
| 19 | 85.165 | | 0.03 | 1621.65 | 231.32 |
| TOTALS | | | 100.00 | 5343381.15 | 384147.01 |

Example 3

Large Scale Batch Production Of Conjugated Safflower FAME

The production of safflower conjugated fatty acid methyl ester (FAME) may be divided into two steps, methanolysis and conjugation. For methanolysis, 6,000 kg safflower oil was drawn into a closed reactor. The reactor was purged with nitrogen at atmospheric pressure, and 1150 liters of methanol and 160 kg of $NaOCH_3$ (30% solution) were added. The mixture is heated to 65° C. while stirring, and reacted at 65° C. for 2 hours. The resulting bottom layer was decanted while the reactor was purged with nitrogen gas. 1000 liters of water (40–50° C., into which 50 kg citric acid monohydrate has been dissolved) was then added while stirring. The layers were allowed to separate (approx. 60 min.) and the bottom layer decanted while purging the reactor with nitrogen gas. The resulting safflower FAME product was dried at 80° C. under vacuum for one hour.

To conjugate the safflower FAME, 250 kg of $KOCH_3$ dissolved in methanol to form a paste was added to the reactor. The mixture was then heated to 120° C. while stirring and the reaction allowed to continue for 3 hours. The mixture was cooled to 100° C., and 1000 liters of water (40–50° C., into which 50 kg citric acid monohydrate has been dissolved) was added while stirring. The mixture was stirred for 15 minutes and then the layers were allowed to separate for 20 minutes. The bottom layer was decanted and the product dried at 80° C. for 1 hour and then stored under nitrogen.

The resulting CLA was analyzed using a Perkin Elmer Autosystem XL GC under the following conditions:

Column: WCOT Fused Silica 100 m×0.25 mm, Coating CP-SIL 88

Carrier: He gas, 30.0 PSI

Temp: 220° C.

Run time: 35–90 min.

Inject.: Splitless, 240° C.

Detect.: FID, 280° C.

The GC results are summarized in Table 3.

TABLE 3

Gas Chromatography Results

| Peak # | Time (Min) | Component Name | Area (%) | Area ($\mu$V.s) | Height ($\mu$V) |
|---|---|---|---|---|---|
| 1 | 46.874 | C16:0 | 6.37 | 29874.50 | 4026.29 |
| 2 | 58.685 | C18:0 | 2.61 | 12231.70 | 1542.34 |
| 3 | 62.141 | C18:1 c9 | 13.14 | 61668.78 | 7369.08 |
| 4 | 62.652 | | 0.70 | 3263.62 | 391.92 |
| 5 | 66.404 | | 0.35 | 1627.60 | 177.41 |
| 6 | 66.917 | | 0.26 | 1239.15 | 157.35 |
| 7 | 67.583 | C18:2 c9,c12 | 5.75 | 26964.95 | 3153.80 |
| 8 | 70.631 | | 0.25 | 1171.90 | 141.41 |
| 9 | 75.011 | CLA c9,t11 | 34.42 | 161529.90 | 17544.79 |
| 10 | 75.936 | CLA t10,c12 | 33.48 | 157129.82 | 17157.21 |
| 11 | 76.400 | CLA c9,c11 | 0.84 | 3935.70 | 302.61 |
| 12 | 76.631 | CLA c10,c12 | 0.49 | 2316.98 | 279.31 |
| 13 | 77.905 | CLA t,t9,11 + 10,12 | 1.35 | 6344.50 | 710.88 |
| | | TOTALS | 100.00 | 469299.10 | 52954.41 |

Example 4

Preparation Of Capsules For Oral Use

In some preferred embodiments, CLA may be combined with anti-hyperglycemic agents. As an example, 2 mg Glimepirid may be formulated with 750 mg CLA 80 in a soft gelatin capsule.

All publications and patents mentioned in the above specification are herein incorporated by reference. Various modifications and variations of the described compositions and methods of the invention will be apparent to those skilled in the art without parting from the scope and spirit of the invention. Although the invention has been described in connection with particular preferred embodiments, it should be understood that the inventions claimed should not be unduly limited to such specific embodiments. Indeed, various modifications of the described modes for carrying out the invention which are obvious to those skilled in the art and in fields related thereto are intended to be within the scope of the following claims.

What is claimed is:

1. A method of treating symptoms of diabetes in a human comprising:
   a) providing
      i) a therapeutically effective amount of conjugated linoleic acid; and
      ii) a human patient suffering from diabetes; and
   b) administering said therapeutically effective amount of conjugated linoleic acid to said human diabetic patient under conditions such that said symptoms of diabetes are treated.

2. The method of claim 1 wherein said diabetic patient is suffering from diabetes selected from the group consisting of Type I diabetes and Type II diabetes.

3. The method of claim 1 wherein said symptom is increased glycosylated hemoglobin and said conjugated linoleic acid is sufficient to reduce the percentage of glycosylated hemoglobin in the blood of said patients.

4. The method of claim 1 wherein said conjugated linoleic acid is a mixture octadecadienoic acid isomers selected from the group of cis-9, trans-11; cis-9, cis-11, trans-9, cis-11; trans-9, trans-11; cis-10, cis-12; cis-10, trans-12; trans-10, cis-12; trans10, trans-12 octadecadienoic acid.

5. The method of claim 1 wherein said conjugated linoleic acid contains less than 5% of minor isomers of conjugated linoleic acid.

6. The method of claim 5 wherein said minor isomer is selected from the group consisting of cis-11, trans-13; trans-11, cis-13; trans-11, trans-13; and cis-11, cis-13 octadecadienoic acid.

7. The method of claim 1 wherein said conjugated linoleic acid contains less than 1% of minor isomers of conjugated linoleic acid.

8. The method of claim 7 wherein said minor isomer is selected from the group consisting of cis-11, trans-13; trans-11, cis-13; trans-11, trans-13; and cis-11, cis-13 octadecadienoic acid.

9. The method of claim 1 wherein said therapeutically effective amount of conjugated linoleic acid comprises a daily dosage of about 0.05 to 40 grams.

10. The method of claim 1 wherein said therapeutically effective amount of conjugated linoleic acid comprises a daily dosage of about 1 to 5 grams.

11. The method of claim 1 wherein said conjugated linoleic acid is administered orally in a gel capsule.

12. The method of claim 9 wherein said conjugated linoleic acid is provided as a supplement to a low carbohydrate diet.

13. The method of claim 9 wherein said conjugated linoleic acid is provided in a prepared food product.

14. The method of claim 1 wherein said conjugated linoleic acid is provided as an ester.

15. The method of claim 1 wherein said conjugated linoleic acid further comprises greater than 55% t10,c12 octadecadienoic acid.

16. The method of claim 1, further comprising co-administering an anti-hyperglycemia agent.

17. The method of claim 16 wherein said anti-hyperglycemia agent is selected from the group consisting of insulin, metformin, chlorpropamide, glipizid, glibenclamide and acarbose.

18. The method of claim 1 wherein said conjugated linoleic acid is provided as a triglyceride or alkyl ester.

19. A method of treating diabetes comprising:
   a) providing
      i) a therapeutically effective amount of conjugated linoleic acid; and
      ii) a human patient suffering from diabetes; and
   b) administering said therapeutically effective amount of conjugated linoleic acid to said human diabetic patient, wherein the percentage of glycosylated hemoglobin in the blood of said human patients is reduced, and wherein said therapeutically effective amount of conjugated linoleic acid comprises a daily dosage of about 0.05 to 40 grams.

20. The method of claim 19 wherein said conjugated linoleic acid is a mixture of octadecadienoic acid isomers selected from the group of cis-9, trans- 11; cis-9, cis-11; trans-9, cis-11,; trans-9, trans-11; cis-10, cis-12; cis-10, trans-12; trans-10, cis-12; trans- 10, trans-12 octadecadienoic acid.

21. The method of claim 19 wherein said conjugated linoleic acid contains less than 5% of minor isomers of conjugated linoleic acid.

22. The method of claim 21 wherein said minor isomer is selected from the group consisting of cis-11, trans-13; trans-11, cis-13; trans-11, trans-13; and cis- 11, cis-13 octadecadienoic acid.

23. The method of claim 19 wherein said therapeutically effective amount of conjugated linoleic acid comprises a daily dosage of about 1 to 5 grams.

24. The method of claim 19 wherein said conjugated linoleic acid is administered orally in a gel capsule.

25. The method of claim 19 wherein said conjugated linoleic acid further comprises greater than 55% t10,c12 octadecadienoic acid.

26. The method of claim 19, further comprising co-administering an anti-hyperglycemia agent.

27. The method of claim 26 wherein said anti-hyperglycemia agent is selected from the group consisting of insulin, metformin, chlorpropamide, glipizid, glibenclamide and acarbose.

28. A method of treatment, comprising:
   a) providing:
      i) a human patient at risk for diabetes, and
      ii) a therapeutic composition comprising an effective amount of conjugated linoleic acid; and
   b) prophylactically administering said therapeutic composition to said human patient under conditions such that the risk of diabetes is reduced, wherein said effective amount of conjugated linoleic acid comprises a daily dosage of about 0.05 to 40 grams.

29. The method of claim 28 wherein said conjugated linoleic acid is a mixture of octadecadienoic acid isomers selected from the group of cis-9, trans-11; cis-9, cis-11; trans-9, cis-11; trans-9, trans-11; cis-10, cis-12; cis-10, trans-12; trans-10, cis-12; trans-10, trans-12 octadecadienoic acid.

30. The method of claim 28 wherein said conjugated linoleic acid contains less than 5% of minor isomers of conjugated linoleic acid.

31. The method of claim 30 wherein said minor isomer is selected from the group consisting of cis-11, trans-13; trans-11, cis-13; trans-11, trans-13; and cis-11, cis-13 octadecadienoic acid.

32. The method of claim 25 wherein said conjugated linoleic acid comprises a daily dosage of about 1 to 5 grams.

33. The method of claim 25 wherein said conjugated linoleic acid is administered orally in a gel capsule.

34. The method of claim 28 wherein said conjugated linoleic acid further comprises greater than 55% t10,c12 octadecadienoic acid.

35. A method of reducing glycosylated hemoglobin in the blood of human diabetic patients comprising:
   a) providing
      i) an anti-hyperglycemia agent and a therapeutically effective amount of conjugated linoleic acid; and
      ii) a human patient suffering from diabetes; and
   b) co-administering said antihyperglycemia agent and said therapeutically effective amount of conjugated linoleic acid to said human diabetic patient under conditions such that the percentage of glycosylated hemoglobin in blood of said human patients is reduced, wherein said therapeutically effective amount of conjugated linoleic acid comprises a daily dosage of about 0.05 to 40 grams.

36. The method of claim 35 wherein said diabetic patient is suffering from diabetes selected from the group consisting of Type I diabetes and Type II diabetes.

37. The method of claim 35 wherein said conjugated linoleic acid is a mixture of octadecadienoic acid isomers selected from the group of cis-9, trans-11; cis-9, cis-11; trans-9, cis-11; trans-9, trans-11; cis-10, cis-12; cis-10, trans-12; trans-10, cis-12; trans-10, trans-12 octadecadienoic acid.

38. The method of claim 35 wherein said conjugated linoleic acid contains less than 5% of minor isomers of conjugated linoleic acid.

39. The method of claim 38 wherein said minor isomer is selected from the group consisting of cis-11, trans-13; trans-11, cis-13; trans-11, trans-13; and cis-11, cis-13 octadecadienoic acid.

40. The method of claim 35 wherein said therapeutically effective amount of conjugated linoleic acid comprises a daily dosage of about 1 to 5 grams.

41. The method of claim 35 wherein said conjugated linoleic acid is administered orally in a gel capsule.

42. The method of claim 35 wherein said conjugated linoleic acid is provided as a supplement to a low carbohydrate diet.

43. The method of claim 35 wherein said conjugated linoleic acid is provided in a prepared food product.

44. The method of claim 35 wherein said conjugated linoleic acid is provided as an ester.

45. The method of claim 35 wherein said anti-hyperglycemia agent is selected from the group consisting of insulin, metformin, chlorpropamide, glipizid, glibenclamide and acarbose.

46. The method of claim 35 wherein said conjugated linoleic acid is provided as a triglyceride or alkyl ester.

* * * * *